(12) United States Patent
Matzger et al.

(10) Patent No.: US 9,353,129 B2
(45) Date of Patent: May 31, 2016

(54) MICROPOROUS COORDINATION COMPLEX AND METHOD OF MAKING THE SAME

(75) Inventors: Adam J. Matzger, Ann Arbor, MI (US); Kyoungmoo Koh, Midland, MI (US)

(73) Assignee: The Regents Of The University Of Michigan, Ann Arbor, MI (US)

( * ) Notice: Subject to any disclaimer, the term of this patent is extended or adjusted under 35 U.S.C. 154(b) by 144 days.

(21) Appl. No.: 14/130,607

(22) PCT Filed: Jul. 6, 2012

(86) PCT No.: PCT/US2012/045700
§ 371 (c)(1),
(2), (4) Date: May 2, 2014

(87) PCT Pub. No.: WO2013/006767
PCT Pub. Date: Jan. 10, 2013

(65) Prior Publication Data
US 2014/0234624 A1    Aug. 21, 2014

Related U.S. Application Data

(60) Provisional application No. 61/504,945, filed on Jul. 6, 2011.

(51) Int. Cl.
*C07F 3/06* (2006.01)
*C07C 63/66* (2006.01)
*C07C 57/15* (2006.01)
(Continued)

(52) U.S. Cl.
CPC . *C07F 3/06* (2013.01); *C07C 57/15* (2013.01); *C07C 63/28* (2013.01); *C07C 63/333* (2013.01); *C07C 63/38* (2013.01); *C07C 63/46* (2013.01); *C07C 63/66* (2013.01); *Y10T 428/2982* (2015.01)

(58) Field of Classification Search
CPC ...... C07C 57/15; C07C 63/28; C07C 63/333; C07C 63/38; C07C 63/46; C07C 63/66; C07F 3/06; Y10T 428/2982
USPC ............................................ 428/402; 556/40
See application file for complete search history.

(56) References Cited

U.S. PATENT DOCUMENTS 8,222,179 B2 * 7/2012 Matzger et al. ............... 502/401
2003/0004364 A1 1/2003 Yaghi et al.
(Continued)

FOREIGN PATENT DOCUMENTS

WO    WO2009/029848    3/2009

OTHER PUBLICATIONS

Yaghi ("Reticular Chemistry and Metal-Organic Frameworks for Clean Energy" MRS Bulletin, vol. 34, Sep. 2009, p. 682-691).*
(Continued)

Primary Examiner — Jafar Parsa
Assistant Examiner — Amy C Bonaparte
(74) Attorney, Agent, or Firm — Harness, Dickey & Pierce, PLC

(57) ABSTRACT

Disclosed herein is a three-dimensional coordination complex that includes a plurality of inorganic centers; a plurality of a first bis(bidentate) linker; and a plurality of a second bis(bidentate) linker, where the first and the second bis(bidentate) linkers are have different lengths, and the bidentate binding sites on each linker face in opposite directions on an axis.

35 Claims, 10 Drawing Sheets

(51) Int. Cl.
*C07C 63/28* (2006.01)
*C07C 63/333* (2006.01)
*C07C 63/38* (2006.01)
*C07C 63/48* (2006.01)
*C07C 63/46* (2006.01)

(56) References Cited

U.S. PATENT DOCUMENTS

| | | | |
|---|---|---|---|
| 2009/0062409 A1* | 3/2009 | Matzger et al. | 521/50 |
| 2009/0178558 A1 | 7/2009 | Hupp et al. | |
| 2009/0306420 A1 | 12/2009 | Schubert et al. | |
| 2010/0075123 A1* | 3/2010 | Masel et al. | 428/219 |
| 2013/0237411 A1* | 9/2013 | Matzger et al. | 502/401 |

OTHER PUBLICATIONS

Matzger ("Coordination Copolymerization Mediated by Zn4O(CO2R)6" JACS, 2010, 132, 15005-15010—published online on Oct. 6, 2010).*

Koh ("A Crystalline Mesoporous Coordination Copolymer with High Microporosity", Angew. Chem. Int. Ed. 2008, 47, 677-680).*

Koh ("Exceptional surface area from coordination copolymers derived from two linear linkers of differing length" Chemical Science (2012), 3, 2429-2432).*

Yao ("Interpenetrated metal-organic frameworks and their uptake of CO2 at relatively low pressures" Journal of Materials Chemistry (2012), 22(20), 10345-10351).*

Gomez et al. (2005). Novel 2D and 3D Indium Metal-Organic Frameworks: Topology and Catalytic Properties. *Chemical Material.* vol. 17. No. 10. pp. 2568-2573.

Yin et al. (2007). Coexistence of Two Aromatic Bicarboxylate Ligands with Distinct Conformations in a Fluorescent Zinc (II) Polymer. *Inorganic Chemistry Communications.* vol. 11. No. 2. pp. 134-137.

Supplemental European Search Report mailed Dec. 17, 2014 for European Patent Application 12806919.2.

Burrows. (2011). Mixed-component metal-organic frameworks (MC-MOFs): enhancing functionality through solid solution formation and surface modifications. *CrystEngComm*, vol. 13, pp. 3623-3642.

International Search Report and Written Opinion mailed Jan. 24, 2013, for PCT/US2012/045700 claiming benefit of U.S. Appl. No. 61/504,945, filed Jul. 6, 2011.

* cited by examiner

US 9,353,129 B2

MICROPOROUS COORDINATION COMPLEX AND METHOD OF MAKING THE SAME

CROSS REFERENCE TO RELATED APPLICATION

This application is a 371 U.S. National Phase application of PCT/US2012/045700, filed Jul. 6, 2012, published in English as WO 2013/006767 A2 on Jan. 10, 2013 and republished with amended claims on May 2, 2013 as WO 2013/006767 A4. This application claims the benefit under 35 U.S.C. §119(e) of U.S. Provisional Patent Application No. 61/504,945, filed Jul. 6, 2011. The entire disclosures of both applications are incorporated herein by reference.

STATEMENT OF GOVERNMENT INTEREST

This invention was made with government support under Grant No. DE-SC0004888 awarded by the U.S. Department of Energy. The government has certain rights in the invention.

BACKGROUND OF THE INVENTION

1. Field of the Disclosure

The disclosure generally relates to highly porous coordination complexes defined by an inorganic center and at least two different bis(bidentate) linkers bound to that center. The complexes can be used, for example, in gas storage, separation and catalysis.

2. Brief Description of Related Technology

Due to the importance of internal surface area in various applications including gas storage, separation, and catalysis, many researchers have made efforts to discover porous materials with high surface areas. Even though thousands of microporous coordination polymers (MCPs) have been reported to date, few materials possess Brunauer-Emmett-Teller (BET) surface areas over 4000 $m^2/g$. Those materials that do possess such high surface areas tend to require organic linkers that are not readily available at reasonable costs.

Benzene-1,4-dicarboxylic acid, also known as terephthalic acid, is used as a monomer for synthesis of various polymers (e.g., polyethylene terephthalate) and as an organic linker in microporous coordination polymers. For example, benzene-1,4-dicarboxylic acid reacts with zinc nitrate to yield $Zn_4O$(benzene-1,4-dicarboxylate)$_3$ (MOF-5), which has a cubic network structure in the Fm3m space group. MOF-5 has been broadly explored in the porous material field. The BET surface area of MOF-5 is approximately 3200 $m^2/g$.

Naphthalene-2,6-dicarboxylic acid reacts with zinc nitrate to yield a material formulated as $Zn_4O$(naphthalene-2,6-dicarboxylate)$_3$ (IRMOF-8), the structure of which is somewhat ambiguous. It has been suggested that IRMOF-8 has an interpenetrated structure and, accordingly, the experimental BET surface area (~1500 $m^2/g$) of IRMOF-8 is much lower than accessible surface area derived from the theoretical non-interpenetrated crystal structure (4390 m2/g).

Generally, the prior art does not sufficiently teach or suggest to one of ordinary skill in the art how to further increase the available surface area of these microporous materials.

SUMMARY OF THE INVENTION

Disclosed herein is a coordination complex and a method of making the same, wherein the complex has a non-interpenetrated structure, high structural stability, and surprisingly high surface area and pore volume.

One embodiment is a three-dimensional coordination complex that is made of a plurality of inorganic centers and a plurality of at least two different bis(bidentate) linkers. The different linkers can have different lengths.

The three-dimensional coordination complex can be made of $Zn_4O$ and benzene-1,4-dicarboxylate and naphthalene-2,6-dicarboxylate linkers, or can be made of $Zn_4O$ and naphthalene-2,6-dicarboxylate and biphenyl-4,4'-dicarboxylate linkers.

These three-dimensional coordination complexes can be made by preparing an admixture of a precursor complex (such as a plurality of inorganic centers) and the two different bis(bidentate) linkers that are present in the admixture in a specified ratio relative to each other, and precipitating the coordination complex formed from the mixture.

Additional features of the invention may become apparent to those skilled in the art from a review of the following detailed description, taken in conjunction with the drawings, the examples, and the appended claims.

BRIEF DESCRIPTION OF THE DRAWING FIGURES

For a more complete understanding of the disclosure, reference should be made to the following detailed description and accompanying drawing wherein.

Figure 9:
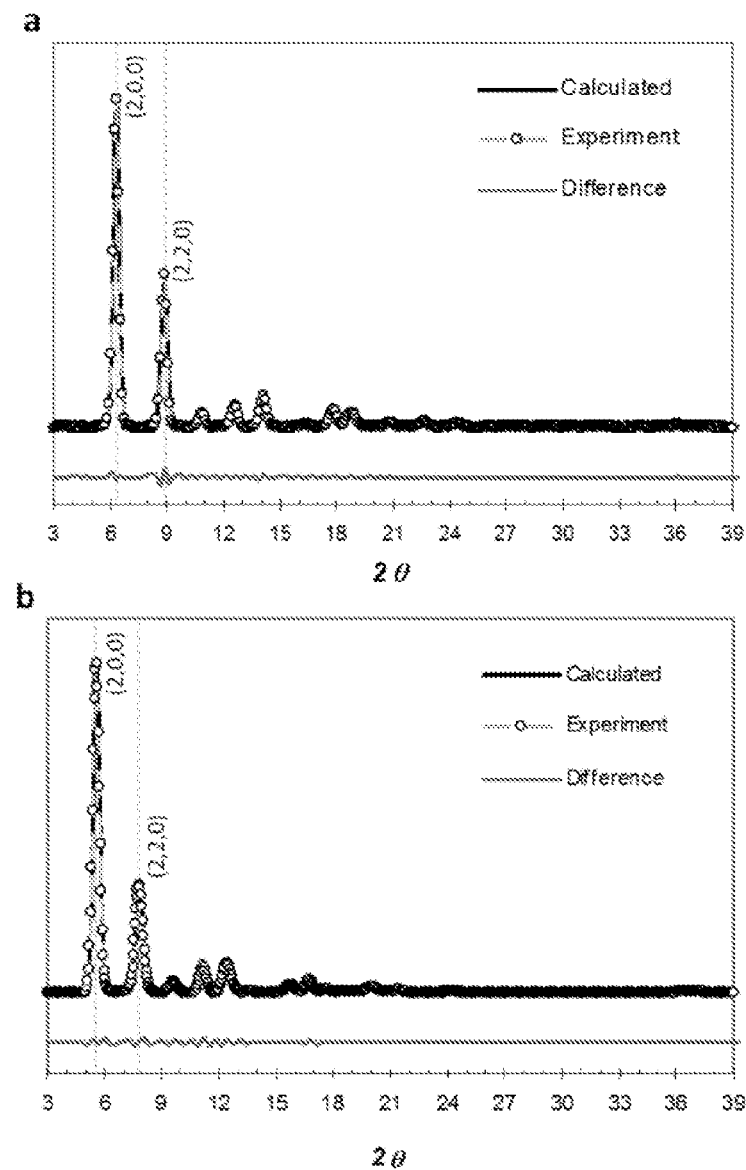
Figure 10:
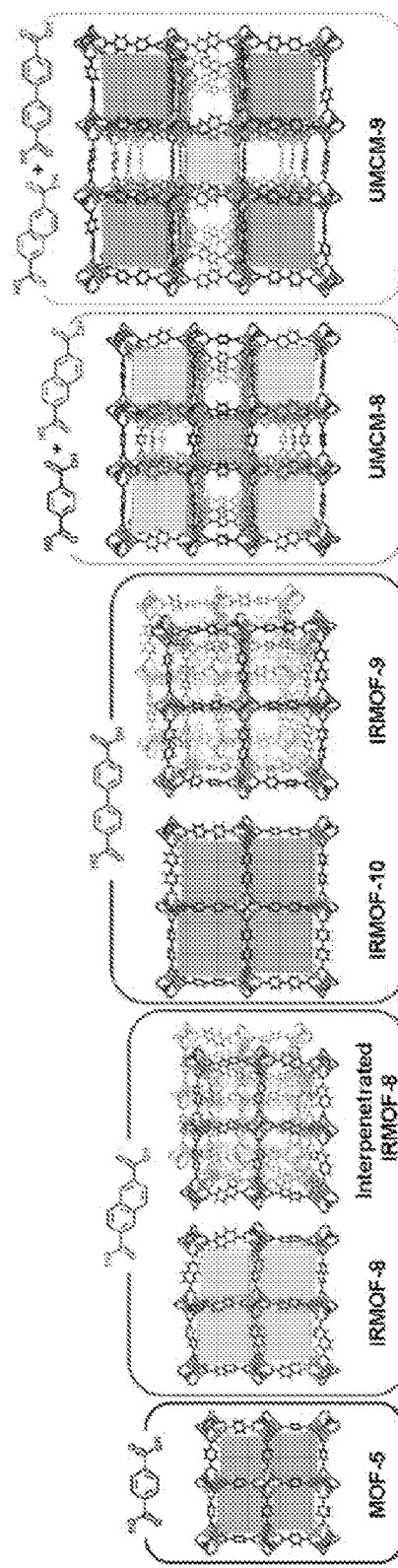

FIG. 9 is a graph of the (a) Pawley refinement results from simulated and experimental powder X-ray diffraction patterns of ($Zn_4O$)(benzene-1,4-dicarboxylate)$_{3/2}$(naphthalene-2,6-dicarboxylate)$_{3/2}$. (b) Pawley refinement results from simulated and experimental powder X-ray diffraction patterns of ($Zn_4O$)(naphthalene-2,6-dicarboxylate)$_{3/2}$(biphenyl-4,4'-dicarboxylate)$_{3/2}$; and, FIG. 10 is a schematic view of the structure comparison of MOF-5, IRMOF-8, 9, and 10 and ($Zn_4O$)(benzene-1,4-dicarboxylate)$_{3/2}$(naphthalene-2,6-dicarboxylate)$_{3/2}$(UMCM-8) and ($Zn_4O$)(naphthalene-2,6-dicarboxylate)$_{3/2}$(biphenyl-4,4'-dicarboxylate)$_{3/2}$(UMCM-9).

While the disclosed complexes and methods are susceptible of embodiments in various forms, there are illustrated in the drawing (and will hereafter be described) specific embodiments of the disclosure, with the understanding that the disclosure is intended to be illustrative, and is not intended to limit the invention to the specific embodiments described and illustrated herein.

DETAILED DESCRIPTION OF THE INVENTION

Conventionally, it is believed that the elongation of an organic linker in the cubic net structure should lead to increasing pore volume and surface area. However, this linear-elongation approach has met with severe limitations with regard to improving surface area. Specifically, expanding free volume is often accompanied by structural interpenetration, which reduces surface area by creating inaccessible regions where two frameworks are in contact. Non-interpenetrated cubic MCPs have been produced by solvothermal reaction under dilute conditions or by a surface-induced method. However, these approaches are not suited to bulk production.

Unexpectedly, it has been found that linear, organic ligands can be utilized to form a homogeneous, non-interpenetrating, stable, microporous material. This is a marked advancement in that it is now possible to prepare microporous materials with unexpectedly high surface area and unexpectedly high pore volume heretofore unattainable. In one specific embodiment, for example, two linear, organic ligands (benzene-1,4-dicarboxylic acid and naphthalene-2,6-dicarboxylic acid) react with zinc nitrate to yield a microporous coordination polymer product with three benzene-1,4-dicarboxylate linkers and three naphthalene-2,6-dicarboxylate linkers coordinated to a $Zn_4O$ cluster. The product has a non-interpenetrated structure and high structural stability after removal of solvent molecules, resulting in surprisingly high surface area and high pore volume.

More generally disclosed herein is a three-dimensional coordination complex that includes a plurality of inorganic centers, a plurality of a first bis(bidentate) linker, and a plurality of a second bis(bidentate) linker. Commonly, coordination complexes including a plurality of inorganic centers are also referred to as coordination polymers. As used herein "coordination complex" refers to compounds having a single inorganic center with linkers bound thereto, as well as compounds having a plurality of inorganic centers with linkers bound thereto, such as a coordination polymer. The first and second bis(bidentate) linkers are bound to the inorganic centers through bidentate binding sites. Preferably, each individual inorganic center is bound to at least one of the first bis(bidentate) linkers and at least one of the second bis(bidentate) linkers. The inorganic centers are preferably cationic. Furthermore, the inorganic centers are preferably hexacoordinate, pentacoordinate, tetracoordinate, or a mixture thereof. In one example the inorganic centers are entirely hexacoordinate.

As described in more detail below, each of the bis(bidentate) linkers has a length. Thus, the first bis(bidentate) linker has a first length. Additionally, the first bis(bidentate) linker can have at least $C_{2h}$ symmetry (theoretical symmetry) where the horizontal σ-plane (implicit in $C_{2h}$ symmetry) contains the bis(bidentate) binding sites. In the coordination complex, the two bidentate binding sites individually bind to different/separate inorganic centers. As used herein, the symmetry descriptions such as "$C_{2h}$" or "σ-plane" refer to the theoretical symmetry of the linker and should be understood to include any distortions in symmetry resulting from coordination.

The second bis(bidentate) linker has a second length, which is different from that of the first length. The second bis(bidentate) linker can have at least one σ-plane that contains the bis(bidentate) binding sites (in the idealized structure). These two bidentate binding sites face in opposite directions along an axis, optionally offset in a transverse direction relative to this axis, as shown, for example, in FIG. 1. In the coordination complex, the second linker's bidentate binding sites each, individually, bind to different/separate inorganic centers.

Figure 1:
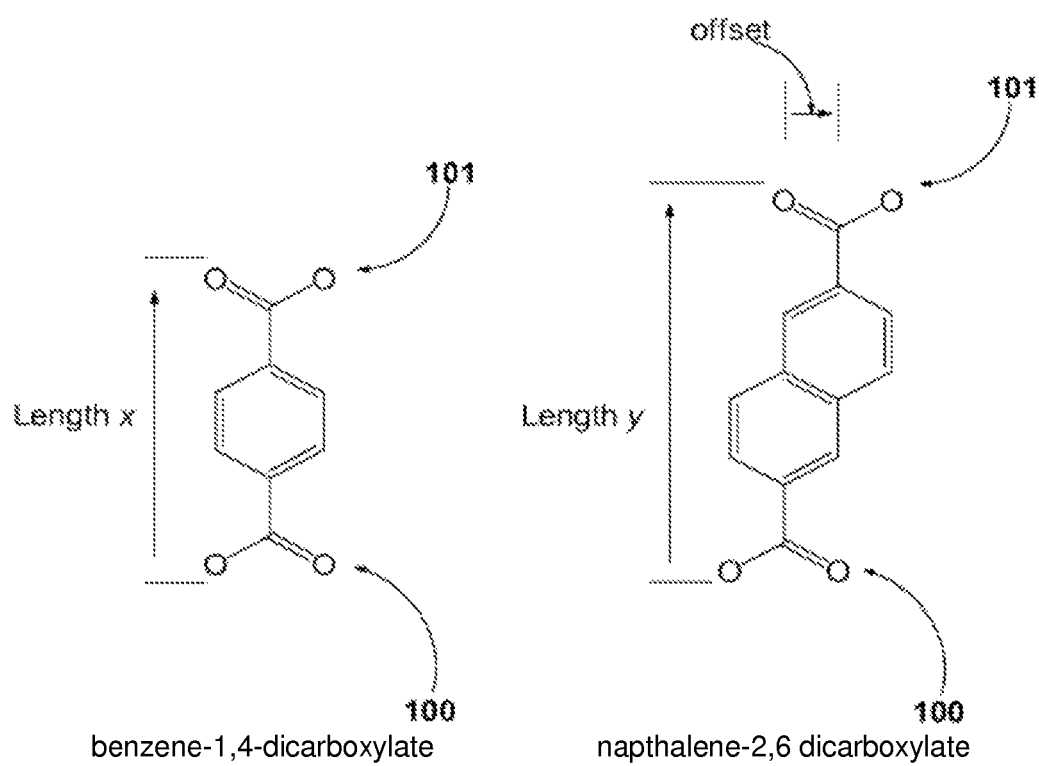
FIG. 1 is a chemical structure image illustrating two bis(bidentate) linkers and the lengths of each.

Herein, the length of the linkers is a measure of the distance between the two bidentate binding sites along an axis irrespective of the offset in a traverse direction relative to that axis. By way of example, FIG. 1 shows the relative lengths of a benzene-1,4-dicarboxylate and a naphthalene-2,6-dicarboxylate. As shown, the length is the minimum distance from a ligate atom of a first bidentate site 100 to a ligate atom of a second bidentate site 101. The first and the second linkers of the coordination complex have different lengths relative to each other and the length of the longer linker (either the first or the second linker) is about 1.1 to about 1.5, more preferably about 1.2 to about 1.4, and even more preferably about 1.3 times the length of the shorter linker (the other of the first or the second linker). In one example, the first bis(bidentate) linker is the longer length bis(bidentate) linker, that is, the first length is longer than the second length. In another example, the second bis(bidentate) linker is the longer length bis(bidentate) linker.

The coordination complex can include the first and second linkers in a ratio from about 1:10 to about 10:1, preferably about 1:5 to about 5:1, more preferably about 1:2 to about 2:1, and even more preferably of about 1:1. In a preferred embodiment, the coordination complex includes the inorganic center : first linker : second linker in a ratio of 2:3:3.

The coordination complex is preferably a mixed coordination complex. A mixed coordination complex includes inorganic centers that have ligands that include both the first bis(bidentate) linker and the second bis(bidentate) linker. The coordination complex can have an inorganic center that is bound to both at least one first bis(bidentate) linker and at least one second bis(bidentate) linker. The coordination complex can be hexacoordinate, that is bound to six ligands, at least two of which include the first and the second bis(bidentate) linkers, preferably at least four of which include the first and second bis(bidentate) linkers, and more preferably at least six of which include the first and second bis(bidentate) linkers. Preferably, the six linkers consist essentially of 1-5 first bis(bidentate) linkers and 1-5 second bis(bidentate) linkers.

Figure 7:
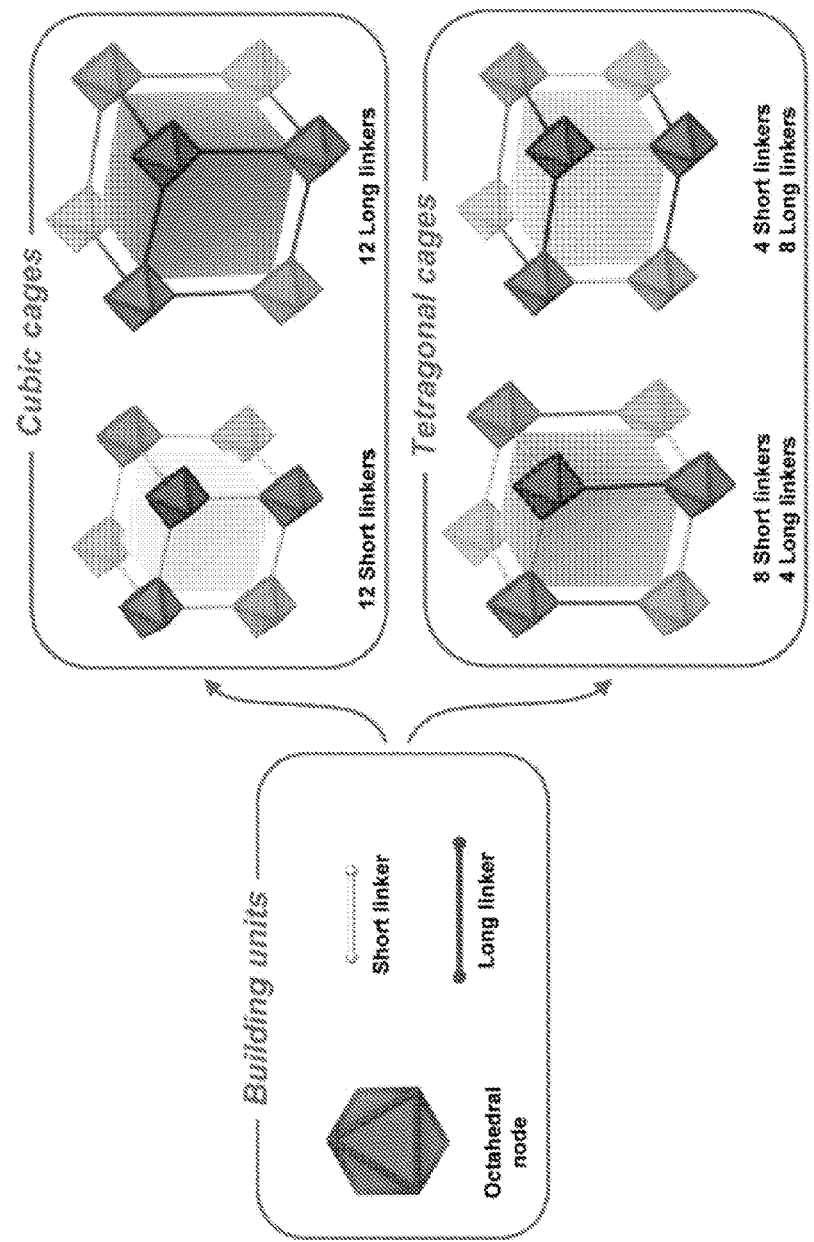
FIG. 7 is a schematic view of cage structures from the assembly of octahedral nodes and two different linear linkers.
Figure 8:
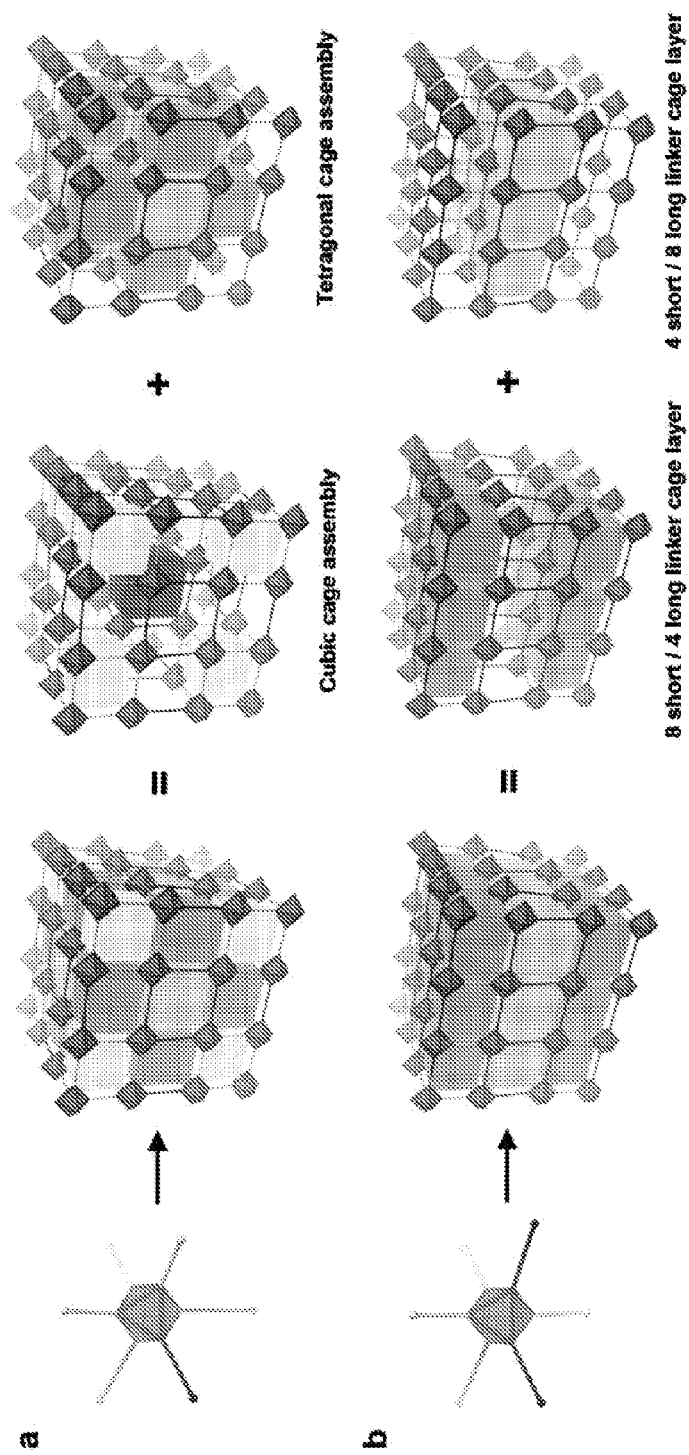
FIG. 8 is a schematic view of the structures resulting from coordination modes with three short linkers and three long linkers coordinated octahedral nodes with facial (a) and meridional (b) fashion.

Exemplary structures are illustrated in FIGS. 7 and 8. As shown in FIG. 7, combining two linear linkers of different lengths with octahedral metal clusters can yield two cubic cages and two tetragonal cages. As shown in FIG. 8, when three short and three long linkers coordinate to an octahedral cluster, two possible coordination modes with meridional and facial fashion can be generated. The framework of the facial coordination mode is built with the assembly of two cubic cages in a corner sharing fashion and the assembly of two tetragonal cages in a face sharing fashion. On the other hand, in the meridional mode the framework is built with two tetragonal cage layers alternating.

As provided above, the inorganic centers are preferably cationic and preferably are hexacoordinate, pentacoordinate, tetracoordinate, or a mixture thereof. Herein, the coordination of the inorganic center is determined by the number of ligands (linkers) that the inorganic center can theoretically bind. While one of ordinary skill may (correctly) argue that the binding of the bidentate linkers requires two coordination sites, as used herein, the number of coordination sites is counted based on the number of linkers supported at the inorganic center in the coordination complex (not the total number of coordination sites). In one example, the inorganic centers are entirely hexacoordinate. One example of an inorganic center that is hexacoordinate is $M_4O$, wherein M is a metal and can be selected from the group including, but not limited to, Zn, Be, Mg, and Co. The $M_4O$ inorganic center coordinates six carboxylates in an octahedron geometry. For example, the hexacoordinate inorganic center can be $Zn_4O$. Another example of a hexacoordinate inorganic center is $M_3O$, wherein M includes, but is not limited to, Fe, Cr, Ru, Mn, V, Ni, Sc, Co, Ir, al, Zn, Ga, Nb, Mo, W, and combinations thereof. The $M_3O$ inorganic center coordinates six carboxylates to form a trigonal prism geometry. Yet another example of a hexacoordinate inorganic center is $M_3$. In some embodiments with an $M_3$ inorganic center, M includes, but is not limited to, Cu, Pd, and combinations thereof and the inorganic center coordinates six carboxylates to form a trigonal prism geometry. In other embodiments with an $M_3$ inorganic center, M includes but is not limited to, Zn, Co, La, Mn, Mg and combinations thereof and the inorganic center coordinates six carboxylates in an octahedral geometry. The inorganic center can also be entirely tetracoordinate. One example of a tetracoordinate inorganic center is $M_2$, wherein M includes, but is not limited to, Ru, Cu, Rh, Mo, Fe, Ni, Co, Re, Cr, Zn, Mn, W, Tc, Os, Cd, Bi, Pt, Al, Mg, In, and combinations thereof. The $M_2$ inorganic center coordinates four carboxylates in a square paddle-wheel geometry. In embodiments including a plurality of inorganic centers, one or more of the inorganic centers can be hexacoordinate, as described above, and/or tetracoordinate, as described above.

The first and the second bis(bidentate) linkers can include ligate atoms selected from oxygen, nitrogen, sulfur, and mixtures thereof. Examples of bidentate functionalities include carboxylates, thiocarboxylates, amides, and thioamides. The bis(bidentate) linkers can have two of the same bidentate functionalities or can have different bidentate functionalities. Examples of suitable bis(bidentate) linkers with the same bidentate functionalities include those of formulas (A)-(H):

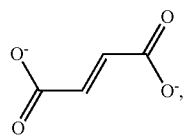

(A)

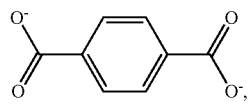

(B)

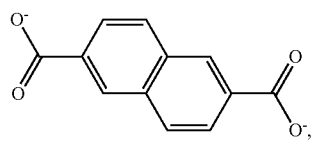

(C)

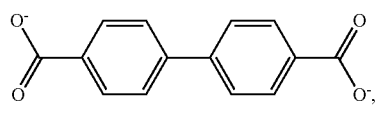

(D)

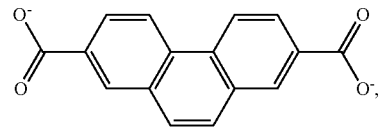

(D')

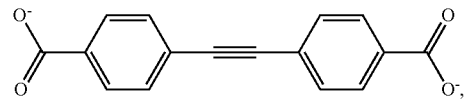

(E)

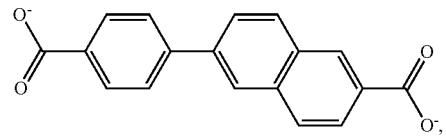

(F)

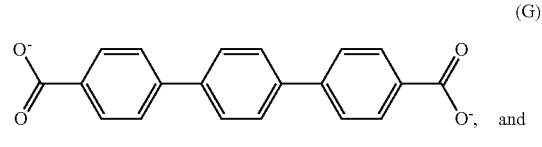

(G)

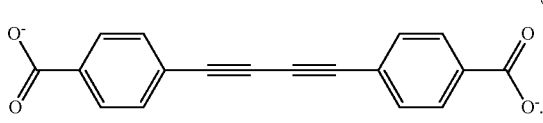

and (H)

With reference to formulas (A)-(H), selection of the first and second linkers can be made such that they have different lengths, as discussed above. For example, the first and second bis(bidentate) linkers can be selected, respectively, from neighboring linkers in the formulas above. For example, the first bis(bidentate) linker can be formula (A) and the second bis(bidentate) linker can be formula (B); first bis(bidentate) linker can be formula (B) and the second bis(bidentate) linker can be formula (A) or (C); first bis(bidentate) linker can be formula (C) and the second bis(bidentate) linker can be formula (B), (D) or (D'); first bis(bidentate) linker can be formula (D) or (D') and the second bis(bidentate) linker can be formula (C), (E) or (F); first bis(bidentate) linker can be formula (E) and the second bis(bidentate) linker can be formula (D), (D'), (F) or (G); first bis(bidentate) linker can be formula (F) and the second bis(bidentate) linker can be formula (E), (G), or (H).

Furthermore, the bis(bidentate) linkers can include functionalities in addition to the requisite two bidentate binding sites. For example, a bis(bidentate) linker can be a benzene-1,4-dicarboxylate of formula (I):

(I)

where R is individually selected from the group consisting of $NH_2$, $NO_2$, $CH_3$, Br, Cl, I, and $OC_{1-8}H_{3-17}$; and x is equal to 0, 1, 2, 3, or 4. When x is equal to zero, of course, the hydrogen atoms on the benzene ring are unsubstituted.

In another example, a bis(bidentate) linker can be a naphthalene-2,6-dicarboxylate of formula (J):

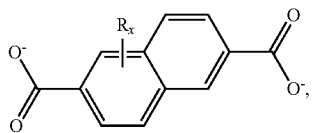

where R is defined above and x can be 0-6. The location of the substitution on the naphthalene rings is not limited by the representative structure shown above. Thus, the functionality can be present at location numbers 1, 3, 4, 5, 7, 8, or combinations thereof, as commonly understood by one of ordinary skill.

In still another example, a bis(bidentate) linker can be a biphenyl-4,4'-dicarboxylate of formula (K):

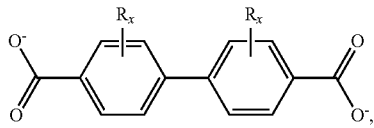

where R is defined above and each x can be 0-4. The location of the substitution on each individual phenyl ring of the biphenyl is not limited by the representative structure shown above. Thus, the functionality can be at location numbers 2, 3, 5, 6, 2', 3', 5', 6' or combinations thereof.

Examples of coordination complexes, include $(Zn_4O)$ (benzene-1,4-dicarboxylate)$_{3/2}$(naphthalene-2,6-dicarboxylate)$_{3/2}$; and $(Zn_4O)$(naphthalene-2,6-dicarboxylate)$_{3/2}$(biphenyl-4,4'-dicarboxylate)$_{3/2}$.

Preferably, the coordination complex is essentially free of a physical admixture of (A) a first crystalline coordination complex that consists of the inorganic center and the first bis(bidentate) linker with (B) a second crystalline coordination complex that consists of the inorganic center and the second bis(bidentate) linker. Thus, the coordination complex is preferably homogeneous and comprises a single phase.

In one example, when the coordination complex is $(Zn_4O)$(benzene-1,4-dicarboxylate)$_{3/2}$(naphthalene-2,6-dicarboxylate)$_{3/2}$, the coordination complex preferably is essentially free of an admixture of $(Zn_4O)$(benzene-1,4-dicarboxylate)$_3$ and $(Zn_4O)$(naphthalene-2,6-dicarboxylate)$_3$. Herein, "essentially free of" means that that composition does not contain micro- or macro-crystalline materials that have the formula $(Zn_4O)$(benzene-1,4-dicarboxylate)$_3$ or $(Zn_4O)$ (naphthalene-2,6-dicarboxylate)$_3$. One way to determine if the coordination complex is essentially free of $(Zn_4O)$(benzene-1,4-dicarboxylate)$_3$ or $(Zn_4O)$(naphthalene-2,6-dicarboxylate)$_3$ is powder X-ray diffraction. The coordination complex is understood to be essentially free of $(Zn_4O)$(benzene-1,4-dicarboxylate)$_3$ or $(Zn_4O)$(naphthalene-2,6-dicarboxylate)$_3$ when the powder X-ray diffraction pattern does not contain diffraction peaks corresponding to $(Zn_4O)$(benzene-1,4-dicarboxylate)$_3$ or $(Zn_4O)$(naphthalene-2,6-dicarboxylate)$_3$ with a relative peak intensity of greater than 5%, 4%, 3%, 2%, or 1% of the "100% peak" (most intense peak).

Preferably, the $(Zn_4O)$(benzene-1,4-dicarboxylate)$_{3/2}$ (naphthalene-2,6-dicarboxylate)$_{3/2}$ coordination complex has powder X-ray diffraction peaks at 6.3 and 8.9 degrees 2θ. More preferably, the coordination complex also has powder X-ray diffraction peaks at 12.6, and 14.1 degrees 2θ.

In another example, when the coordination complex is $(Zn_4O)$(naphthalene-2,6-dicarboxylate)$_{3/2}$(biphyenyl-4,4'-dicarboxylate)$_{3/2}$, the coordination complex preferably is essentially free of an admixture of $(Zn_4O)$(naphthalene-2,6-dicarboxylate)$_3$ and $(Zn_4O)$(biphenyl-4,4'-dicarboxylate)$_3$. Preferably, the $(Zn_4O)$(naphthalene-2,6-dicarboxylate)$_{3/2}$ (biphyenyl-4,4'-dicarboxylate)$_{3/2}$ coordination complex has powder X-ray diffraction peaks at 5.5 and 7.8 degrees 2θ. More preferably, the coordination complex also has powder X-ray diffraction peaks at 9.5, and 11.0 degrees 2θ.

In another aspect of this embodiment, the coordination complex has an open/porous structure. One method for determining the porosity of the coordination complex is through a Brunauer Emmett Teller (BET) surface area measurement. The coordination complex preferably has a BET surface area of at least 3000 $m^2/g$, and more preferably at least 3500 $m^2/g$. Another method of determining the porosity of the coordination complex is through nitrogen uptake measurements. The coordination complex preferably has a $N_2$ uptake at 77K of at least 800 $cm^3/g$, more preferably 850 $cm^3/g$, even more preferably 900 $cm^3/g$, and still more preferably 950 $cm^3/g$. More preferably, the maximum $N_2$ uptake at 77 K is greater than 800 $cm^3/g$, more preferably 850 $cm^3/g$, even more preferably 900 $cm^3/g$, and still more preferably 950 $cm^3/g$.

A first specific embodiment is a crystalline, porous, homogeneous composition comprising a plurality of $Zn_4O$ clusters; a plurality of benzene-1,4-dicarboxylate each individually bound to the plurality of $Zn_4O$ clusters; and a plurality of naphthalene-2,6-dicarboxylate each individually bound to the plurality of $Zn_4O$ clusters. This crystalline, porous, homogeneous composition, preferably, has powder X-ray diffraction peaks at 6.3 and 8.9 degrees 2θ, and more preferably has additional powder X-ray diffraction peaks at 12.6, and 14.1 degrees 2θ.

A second specific embodiment is a crystalline, porous, homogeneous composition comprising a plurality of $Zn_4O$ clusters; a plurality of naphthalene-2,6-dicarboxylate each individually bound to the plurality of $Zn_4O$ clusters; and a plurality of biphenyl-4,4'-dicarboxylate each individually bound to the plurality of $Zn_4O$ clusters. This crystalline, porous, homogeneous composition, preferably, has powder X-ray diffraction peaks at 5.5 and 7.3 degrees 2θ, and more preferably has additional powder X-ray diffraction peaks at 9.5, and 11.0 degrees 2θ.

Each first and second specific embodiments, individually and preferably, has a BET surface area of at least 3000 $m^2/g$, more preferably at least 3500 $m^2/g$. Furthermore, each first and second specific embodiments, individually and preferably, has a $N_2$ uptake at 77 K of at least 800 $cm^3/g$, more preferably 850 $cm^3/g$, even more preferably 900 $cm^3/g$, and still more preferably 950 $cm^3/g$.

The above described coordination complexes can be made by preparing an admixture of (A) a salt, acid, or ester of a first bis(bidentate) linker, (B) a salt, acid, or ester of a second bis(bidentate) linker, (C) a precursor complex, and, preferably, (D) a solvent; and precipitating the three-dimensional coordination complex. Alternative methods can include the application of a voltage sufficient to drive an electrochemical reaction (e.g., to oxidize or reduce the precursor complex) or the application of radiation (e.g., visual or UV light) sufficient to drive a photochemical reaction. Precipitating the three-dimensional coordination complex can include maintaining reaction conditions for a sufficient period of time to permit the three-dimensional coordination complex to form and deposit as a crystalline material, adding precipitant (e.g., a solution that includes a base), or cooling the solution to a temperature sufficient to reduce the solubility and deposit the three-dimensional coordination complex. A further step in the method can include removing solvent present in the precipitated, three-dimensional coordination complex.

In this embodiment, the precursor complex is a metal containing material that is included in the inorganic centers of the three-dimensional coordination complex. The precursor complex can be a metal salt (e.g., zinc salts, including zinc nitrate, zinc sulfate, zinc chloride or zinc hydroxide) or a metal cluster (e.g., $Zn_4O(benzoate)_6$). The first and the second bis(bidentate) linkers can be provided as salts, acids, or esters of the respective anionic bis(bidentate) linker. One of ordinary skill will appreciate that salts or acids of the anionic bis(bidentate) linker requires a cationic atom or molecule to balance the charge. The cationic atom can be a proton ($H^+$), $Na^+$, $K^+$, $NR_4^+$, $PR_4^+$, or mixtures thereof (where R is a proton or an organic fragment, e.g., $CH_3$, $C_2H_5$, $C_4H_{11}$, $C_6H_5$, or a mixture thereof). Specific examples include the benzene-1,4-dicarboxylic acid, naphthalene-2,6-dicarboxylic acid, and biphenyl-4,4'-dicarboxylic acid.

EXAMPLES

The following examples are provided to illustrate the invention, but are not intended to limit the scope thereof.

Example 1

Benzene-1,4-dicarboxylic acid (0.184 g, 1.11 mmol) and naphthalene-2,6-dicarboxylic acid (0.239 g, 1.11 mmol) were dissolved in 100 mL of N,N-diethylformamide and the solution was clarified by filtration. $Zn(NO_3)_2 \cdot 6H_2O$ (1.70 g, 5.72 mmol) was added to the solution. The mixture was sonicated for 15 min and heated to 85° C. After 1 day, crystals of a single phase were obtained. After cooling to room temperature the product was isolated by decanting the mother liquor and washing with N,N-dimethylformamide (3×100 mL). The resulting solid was then immersed in 100 mL $CH_2Cl_2$ for 2 days, during which time the $CH_2Cl_2$ was replaced three times. The solvent was removed under vacuum at room temperature, yielding the porous material.

Characterization of the prepared materials was by visual inspection, powder X-ray diffraction, $N_2$ uptake, BET surface area measurement, and NMR:

$N_2$ Uptake: $N_2$ adsorption/desorption isotherms were measured volumetrically at 77 K in the range $1.00 \times 10^{-5} \leq P/P_0 \leq 1.00$ with an Autosorb-1 C outfitted with the micropore option by Quantachrome Instruments (Boynton Beach, Fla. USA), running version 1.2 of the ASWin software package. Ultra-high purity He (99.999%, for void volume determination) and $N_2$ (99.999%) were purchased from Cryogenic Gasses and used as received. The sample exchanged with $CH_2Cl_2$ was charged into a sample cell and dried under vacuum (<0.1 millitorr) at room temperature. The resulting mass of dried material in the cell was ~10 mg.

BET Surface Area: The BET surface area values were calculated from the $N_2$ uptake data (W) (above). The data was plotted according to equation (1):

$$1/[W(P_0/P-1)] = 1/W_mC + [(C-1)/W_mC]*(P/P_0) \quad (1)$$

where P and $P_0$ are the equilibrium and saturation pressures of $N_2$ at 77K (as determined from the $N_2$ uptake data); W is the quantity of absorbed $N_2$, and $W_m$ is the quantity of gas absorbed as a monolayer; C is the BET constant. In the BET plot of $1/[W(P_0/P-1)]$ vs. $P/P_0$, the slope and the intercept were used to calculate $W_m$. The total surface area was then calculated based on the equation $S_{total} = (W_m N \cdot s)/V$ where N is Avagadro's number, s is the adsorption cross section, and V is the molar volume of absorbed gas.

Figure 2:
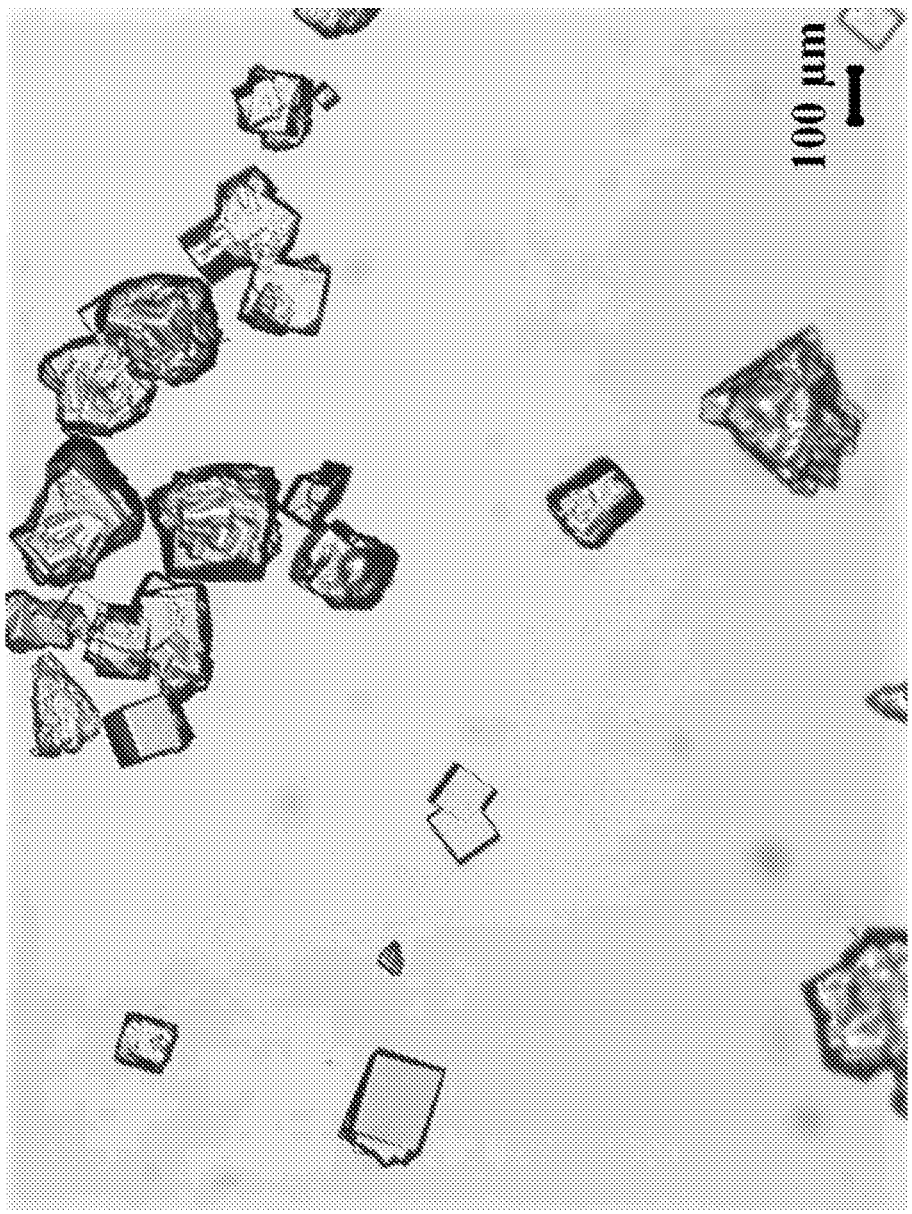
FIG. 2 is an optical microscope image of ($Zn_4O$)(benzene-1,4-dicarboxylate)$_{3/2}$(naphthalene-2,6-dicarboxylate)$_{3/2}$.

FIG. 2 is a photograph of the cubic crystals of the prepared material which is has the formula $(Zn_4O)(benzene-1,4-dicarboxylate)_{3/2}(naphthalene-2,6-dicarboxylate)_{3/2}$ highlighting the stability of the material after removal of the intercalated solvent molecules.

Figure 3:
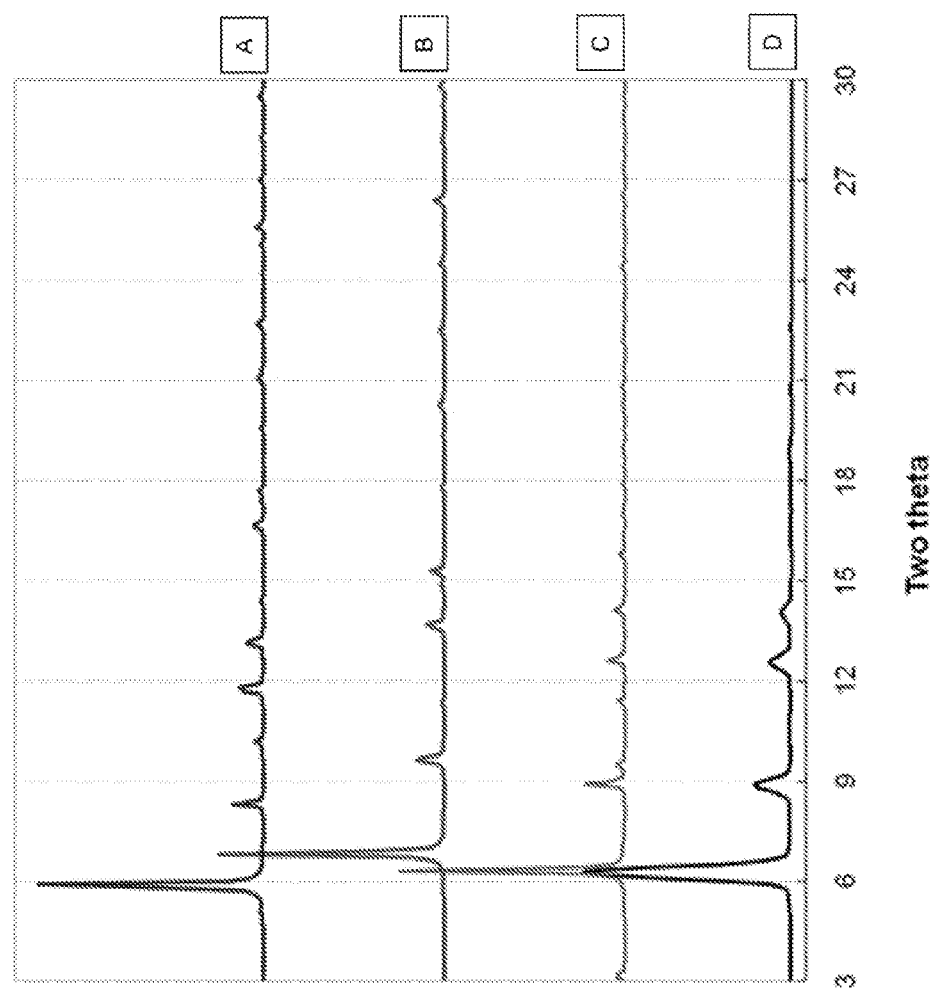
FIG. 3 is a powder X-ray diffraction image illustrating powder X-ray diffraction patterns for IRMOF-8 (plot line A), MOF-5 (plot line B), and simulated pattern (plot line C), and experimental pattern (plot line D) of ($Zn_4O$)(benzene-1,4-dicarboxylate)$_{3/2}$(naphthalene-2,6-dicarboxylate)$_{3/2}$.

FIG. 3 shows plots of powder X-ray diffraction patterns. FIG. 3a is the powder X-ray diffraction pattern for $(Zn_4O)(benzene-1,4-dicarboxylate)_3$. FIG. 3b is the powder X-ray diffraction pattern for $(Zn_4O)(naphthalene-2,6-dicarboxylate)_3$. FIG. 3c is a theoretical powder X-ray diffraction pattern for $[(Zn_4O)(benzene-1,4-dicarboxylate)_{3/2}(naphthalene-2,6-dicarboxylate)_{3/2}]$. FIG. 3d is an experimental powder X-ray diffraction pattern for $[(Zn_4O)(benzene-1,4-dicarboxylate)_{3/2}(naphthalene-2,6-dicarboxylate)_{3/2}]$.

Figure 4:
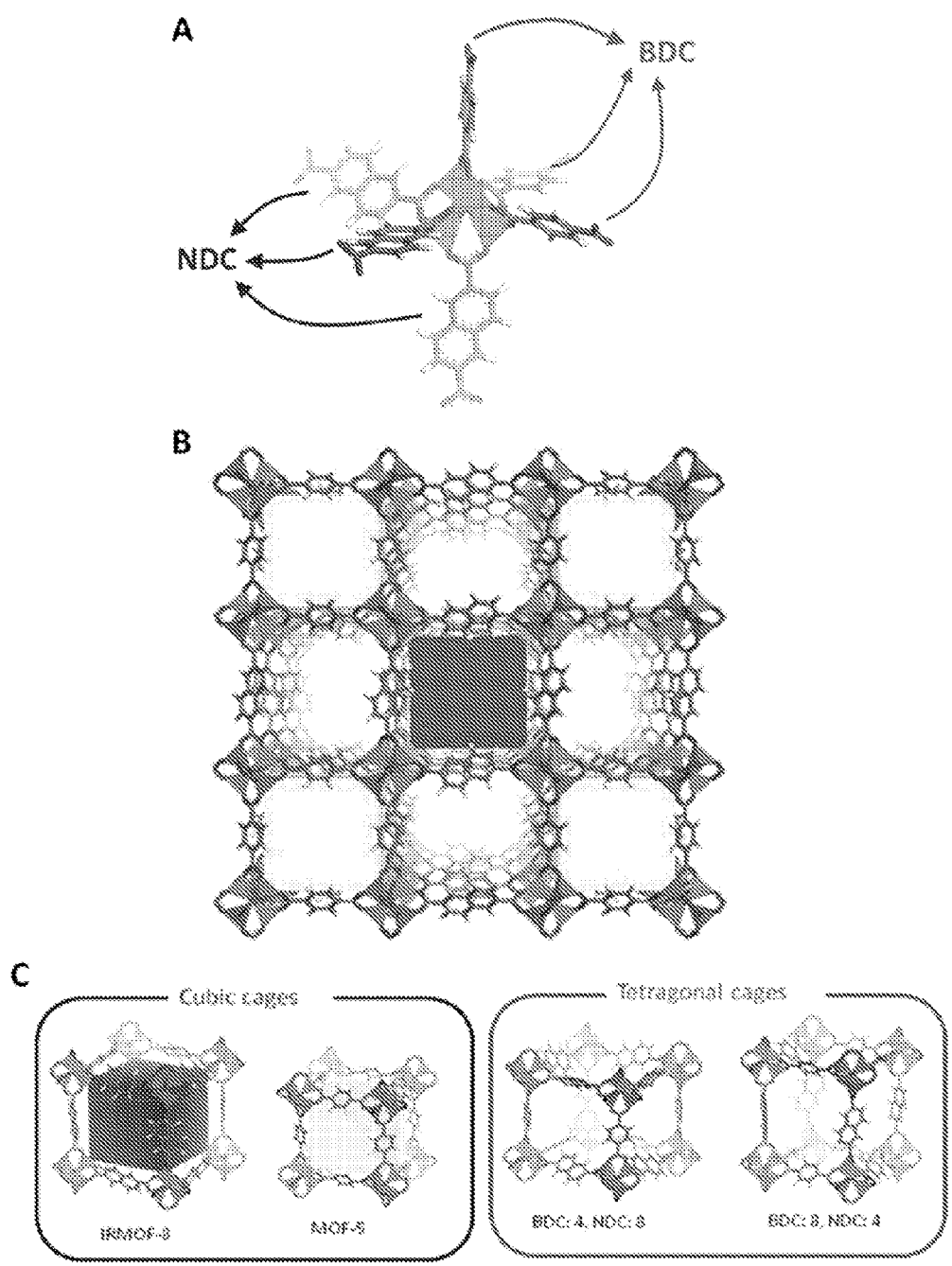
FIG. 4a is a schematic view of the basic zinc acetate cluster ($Zn_4O$) surrounded by 3 benzene dicarboxylate linkers and 3 naphthalene dicarboxylate linkers.
FIG. 4b is a schematic view of structure of ($Zn_4O$)(benzene-1,4-dicarboxylate)$_{3/2}$(naphthalene-2,6-dicarboxylate)$_{3/2}$.
FIG. 4c is a schematic view of microporous cages.

FIG. 4 shows depictions of the structure of $(Zn_4O)(benzene-1,4-dicarboxylate)_{3/2}(naphthalene-2,6-dicarboxylate)_{3/2}$ determine by Pawley refinement of the powder X-ray diffraction data. FIG. 4a shows an inorganic center that has a facial arrangement of three benzene-1,4-dicarboxylate linkers and three naphthalene-2,6-dicarboxylate linkers arranged in an octahedral orientation. FIG. 4b shows the structure $(Zn_4O)(benzene-1,4-dicarboxylate)_{3/2}(naphthalene-2,6-dicarboxylate)_{3/2}$ as a corner-sharing arrangement of MOF-5 cages and IRMOF-8 cages. FIG. 4c shows the structures of the individual cages within the $(Zn_4O)(benzene-1,4-dicarboxylate)_{3/2}(naphthalene-2,6-dicarboxylate)_{3/2}$ structure.

Figure 5:
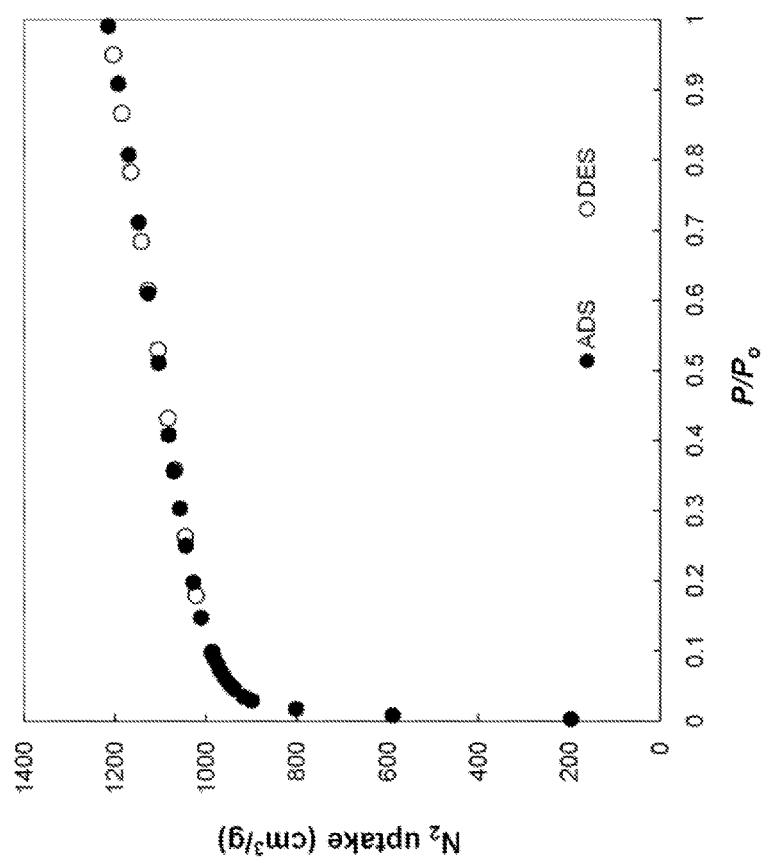
FIG. 5 is a graph plotting a $N_2$ sorption isotherm of ($Zn_4O$)(benzene-1,4-dicarboxylate)$_{3/2}$(naphthalene-2,6-dicarboxylate)$_{3/2}$ at 77K.

FIG. 5 shows the $N_2$ uptake data at 77 K of $(Zn_4O)(benzene-1,4-dicarboxylate)_{3/2}(naphthalene-2,6-dicarboxylate)_{3/2}$. The isotherm can be classified as a type I isotherm.

The Brunauer-Emmett-Teller (BET) surface area is 4030 $m^2/g$ and this value matched well with the theoretical surface area (approximately 4040 $m^2/g$) calculated from the crystal structure.

The composition of linkers in the product was confirmed by the following procedure: the fully dried compounds were decomposed in 1 M NaOH in $D_2O$ solution. The decomposed sample was characterized by $^1H$ NMR. Using the singlet peak at 7.60 ppm resulted from 4H of benzene-1,4-dicarboxylate, and two doublet peaks at 7.70 ppm and 7.80 ppm and one singlet peak at 8.16 ppm resulted from 2H of naphthalene-2,6-dicarboxylate, the composition of the compounds was evaluated and the experimental composition of two linkers matched well with the theoretical value from the crystal structure.

Figure 6:
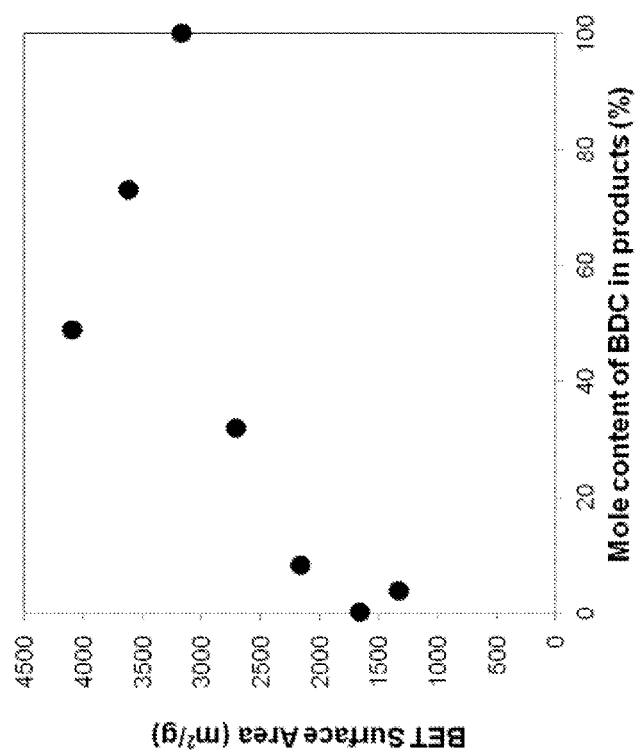
FIG. 6 is a graph plotting BET surface areas of products prepared from various mole fractions of $H_2BDC$ and $H_2NDC$ in the presence of zinc nitrate.

FIG. 6 is a graph showing the BET surface areas of products prepared from various mole fractions of benzene-1,4-dicarboxylic acid ($H_2BDC$) and naphthalene-2,6-dicarboxylic acid ($H_2NDC$) in the presence of zinc nitrate.

Example 2

Naphthalene-2,6-dicarboxylic acid (28.7 mg, 0.13 mmol) and biphenyl-4,4'-dicarboxylic acid (35.6 mg, 0.15 mmol) were dissolved in the mixture of 6.7 mL of N,N-diethylformamide and 13.3 mL of N-methylpyrrolidone, and the solution was clarified by filtration. $Zn(NO_3)_2 \cdot 6H_2O$ (0.238 g, 0.800 mmol) was added to the solution. The mixture was sonicated for 15 min and heated to 85° C. After 4 days, crystals of a single phase were obtained. After cooling to room temperature the product was isolated by decanting the mother liquor and washing with N,N-dimethylformamide (3×20 mL). The resulting solid was then immersed in 20 mL $CH_2Cl_2$ for 2 days, during which time the $CH_2Cl_2$ was replaced three times. Activation was performed with a Jasco PU-1580-CO₂ delivery pump equipped with a back pressure regulator (Jasco-1580-81). The $CH_2Cl_2$ soaked sample was placed in a metal column and $CH_2Cl_2$ was exchanged with liquid $CO_2$ at 100 bar. The liquid $CO_2$ charged column was heated at 35° C. for 30 min. $CO_2$ was vented over 30 minutes via a back pressure regulator to obtain an activated three-dimensional coordination polymer.

The Brunauer-Emmett-Teller (BET) surface area of the resulting material was 4970 m²/g, which corresponded well with the theoretical surface area (4900 m²/g) calculated from the crystal structure.

FIG. 9b shows the Pawley refinement results from simulated and experimental powder X-ray diffraction patterns of $(Zn_4O)$(naphthalene-2,6-dicarboxylate)$_{3/2}$(biphenyl-4,4'-dicarboxylate)$_{3/2}$.

The foregoing description is given for clearness of understanding only, and no unnecessary limitations should be understood therefrom, as modifications within the scope of the invention may be apparent to those having ordinary skill in the art.

What is claimed is:

1. A three-dimensional coordination complex comprising:
    a plurality of inorganic centers;
    a plurality of a first bis(bidentate) linker having a first length and two bidentate binding sites; and
    a plurality of a second bis(bidentate) linker having a second length and two bidentate binding sites,
    wherein each of the first and the second bis(bidentate) linkers is selected from the group consisting of:

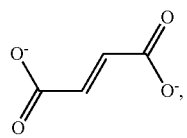
(A)

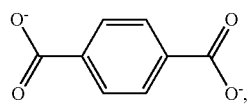
(B)

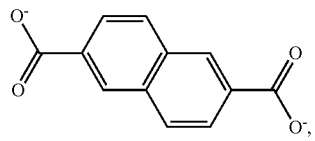
(C)

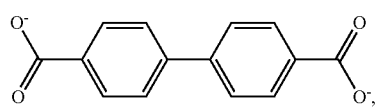
(D)

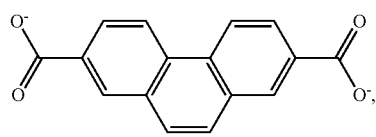
(D')

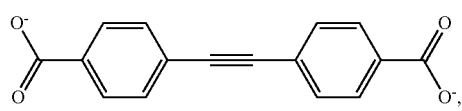
(E)

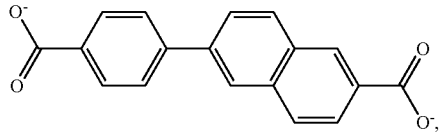
(F)

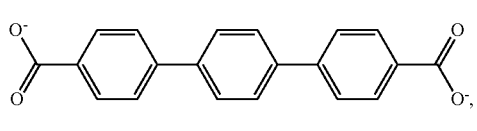
(G)

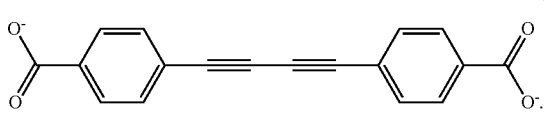
(H)

with the following provisos that where the first or second bis(bidentate) linker has the structure of:
(i) Formula (A), the other linker has the structure of Formula (B);
(ii) Formula (B), the other linker has the structure of Formula (A) or (C);
(iii) Formula (C), the other linker has the structure of Formula (B), (D), or (D');
(iv) Formula (D) or (D'), the other linker has the structure of Formula (C), (E), or (F);
(v) Formula (E) or (F), the other linker has the structure of Formula (D), (D'), or (G);
(vi) Formula (G), the other linker has the structure of Formula (E), (F) or (H); and,
(vii) Formula (H), the other linker has the structure of Formula (G).

2. The three-dimensional coordination complex of claim 1, wherein the inorganic centers are cationic.

3. The three-dimensional coordination complex of claim 2, wherein the inorganic centers are hexacoordinate or tetracoordinate.

4. The three-dimensional coordination complex of claim 3, wherein at least one of the inorganic centers is hexacoordinate, having the formula $M_4O$, wherein M is selected from the group consisting of Zn, Be, Mg, Co, and combinations thereof.

5. The three-dimensional coordination complex of claim 3, wherein at least one of the inorganic centers is hexacoordinate, having the formula $M_3O$, wherein M is selected from the group consisting of Fe, Cr, Ru, Mn, V, Ni, Sc, Co, Ir, Al, Zn, Ga, Nb, Mo, W, and combinations thereof.

6. The three-dimensional coordination complex of claim 3, wherein at least one of the inorganic centers is hexacoordinate, having the formula $M_3$, wherein M is selected from the group consisting of Cu, Pd, Zn, Co, La, Mn, Mg, and combinations thereof.

7. The three-dimensional coordination complex of claim 3, wherein at least one of the inorganic centers is tetracoordinate, having the formula $M_2$, wherein M is selected from the group consisting of Ru, Cu, Rh, Mo, Fe, Ni, Co, Re, Cr, Zn, Mn, W, Tc, Os, Cd, Bi, Pt, Al, Mg, In, and combinations thereof.

8. The three-dimensional coordination complex of claim 1 comprising a ratio of 2:3:3 of inorganic centers :first bis(bidentate) linker :second bis(bidentate) linker.

9. The three-dimensional coordination complex of claim 1, wherein the longer of the first and second lengths is about 1.2 to about 1.4 times longer than the shorter of the first and second lengths.

10. The three-dimensional coordination complex of claim 9, wherein the longer of the first and second lengths is about 1.3 times longer than the shorter of the first and second lengths.

11. The three-dimensional coordination complex of claim 2, wherein the inorganic center is Zn$_4$O.

12. A three-dimensional coordination complex comprising:
   a plurality of inorganic centers;
   a plurality of a first bis(bidentate) linker; and,
   a plurality of a second bis(bidentate) linker,
   wherein the first bis(bidentate) linker comprises a benzene-1,4-dicarboxylate of formula (I):

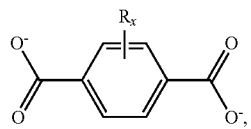

(I)

where R is individually selected from the group consisting of NH$_2$, NO$_2$, CH$_3$, Br, Cl, I, and OC$_{1-8}$H$_{3-17}$; and x is equal to 0, 1, 2, 3, or 4, and wherein the second bis(bidentate) linker comprises a naphthalene-2,6-dicarboxylate of formula (J):

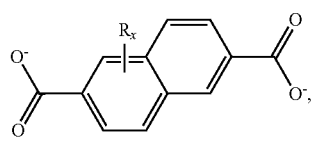

(J)

where R is individually selected from the group consisting of NH$_2$, NO$_2$, CH$_3$, Br, Cl, I, and OC$_{1-8}$H$_{3-17}$; and x is equal to 0, 1, 2, 3, 4, 5, or 6.

13. The three-dimensional coordination complex of claim 1, wherein the coordination complex is (Zn$_4$O)(benzene-1,4-dicarboxylate)$_{3/2}$(naphthalene-2,6-dicarboxylate)$_{3/2}$.

14. The three-dimensional coordination complex of claim 13, wherein the coordination complex is essentially free of an admixture of (Zn$_4$O)(benzene-1, 4-dicarboxylate)$_3$ and (Zn$_4$O)(naphthalene-2,6-dicarboxylate)$_3$.

15. The three-dimensional coordination complex of claim 13, wherein the coordination complex has powder X-ray diffraction peaks at 6.3 and 8.9 degrees 2θ.

16. The three-dimensional coordination complex of claim 15, wherein the coordination complex further has powder X-ray diffraction peaks at 12.6, and 14.1 degrees 2θ.

17. A three-dimensional coordination complex comprising:
   a plurality of inorganic centers;
   a plurality of a first bis(bidentate) linker; and,
   a plurality of a second bis(bidentate),
   wherein the first bis(bidentate) linker comprises a naphthalene-2,6-dicarboxylate of formula (J):

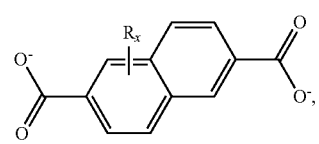

(J)

where R is selected from the group consisting of NH$_2$, NO$_2$, CH$_3$, Br, Cl, I, and OC$_{1-8}$H$_{3-17}$; and x is equal to 0, 1, 2, 3, 4, 5, or 6, and wherein the second bis(bidentate) linker comprises a biphenyl-4,4'-dicarboxylate of formula (K):

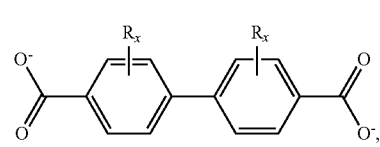

(K)

where R is individually selected from the group consisting of NH$_2$, NO$_2$, CH$_3$, Br, Cl, I, and OC$_{1-8}$H$_{3-17}$; and x is equal to 0, 1, 2, 3, or 4.

18. The three-dimensional coordination complex of claim 17, wherein the coordination complex is essentially free of an admixture of (Zn$_4$O) (naphthalene-2,6-dicarboxylate)$_3$ and (Zn$_4$O)biphenyl-4,4'-dicarboxylate)$_3$.

19. The three-dimensional coordination complex of claim 17, wherein the coordination complex has powder X-ray diffraction peaks at 5.5 and 7.8 degrees 2θ.

20. The three-dimensional coordination complex of claim 19, wherein the coordination complex further has powder X-ray diffraction peaks at 9.5, and 11.0 degrees 2θ.

21. The three-dimensional coordination complex of claim 1, wherein the coordination complex has a Brunauer Emmett Teller (BET) surface area of at least 3000 m$^2$/g.

22. The three-dimensional coordination complex of claim 21, wherein the coordination complex has a BET surface area of at least 3500 m$^2$/g.

23. The three-dimensional coordination complex of claim 21, wherein the coordination complex has a maximum N$_2$ uptake of at least 800 cm$^3$/g at 77 K.

24. The three-dimensional coordination complex of claim 23, wherein the coordination complex has a maximum N$_2$ uptake of at least 850 cm$^3$/g at 77 K.

25. The three-dimensional coordination complex of claim 24, wherein the coordination complex has a maximum N$_2$ uptake of at least 900 cm$^3$/g at 77 K.

26. The three-dimensional coordination complex of claim 25, wherein the coordination complex has a maximum N$_2$ uptake of at least 950 cm$^3$/g at 77 K.

27. The three-dimensional coordination complex of claim 1, wherein the coordination complex is homogeneous and comprises a single phase.

28. A crystalline, porous, homogeneous composition comprising:
   a plurality of Zn$_4$O clusters;
   a plurality of benzene-1,4-dicarboxylate each individually bound to the plurality of Zn$_4$O clusters; and,
   a plurality of naphthalene-2,6-dicarboxylate each individually bound to the plurality of Zn$_4$O clusters.

29. The crystalline, porous, homogeneous composition of claim 28 having powder X-ray diffraction peaks at 6.3 and 8.9 degrees 2θ.

30. The crystalline, porous, homogeneous composition of claim 29 further having powder X-ray diffraction peaks at 12.6, and 14.1 degrees 2θ.

31. A crystalline, porous, homogeneous composition comprising:
a plurality of $Zn_4O$ clusters;
a plurality of naphthalene-2,6-dicarboxylate each individually bound to the plurality of $Zn_4O$ clusters; and,
a plurality of biphenyl-4,4'-dicarboxylate each individually bound to the plurality of $Zn_4O$ clusters.

32. The crystalline, porous, homogeneous composition of claim 31, wherein the composition has powder X-ray diffraction peaks at 5.5 and 7.3 degrees 2θ.

33. The crystalline, porous, homogeneous composition of claim 32, wherein the composition further has powder X-ray diffraction peaks at 9.5, and 11.0 degrees 2θ.

34. The crystalline, porous, homogeneous composition of claim 31, wherein the composition has a BET surface area of at least 3000 $m^2/g$.

35. The crystalline, porous, homogeneous composition of claim 31, wherein the composition has a maximum $N_2$ uptake of at least 800 $cm^3/g$ at 77 K.

\* \* \* \* \*